United States Patent
Yang

(10) Patent No.: US 6,525,317 B1
(45) Date of Patent: Feb. 25, 2003

(54) REDUCTION OF CHARGING EFFECT AND CARBON DEPOSITION CAUSED BY ELECTRON BEAM DEVICES

(75) Inventor: Baorui Yang, Pflugerville, TX (US)

(73) Assignee: Micron Technology Inc., Boise, ID (US)

( * ) Notice: Subject to any disclaimer, the term of this patent is extended or adjusted under 35 U.S.C. 154(b) by 0 days.

(21) Appl. No.: 09/222,999

(22) Filed: Dec. 30, 1998

(51) Int. Cl.$^7$ ............................................. G01N 23/00
(52) U.S. Cl. ....................................... 250/310; 290/306
(58) Field of Search ................................ 250/310, 252, 250/307, 306

(56) References Cited

U.S. PATENT DOCUMENTS

| | | | |
|---|---|---|---|
| 4,140,576 A | * 2/1979 | Fink et al. | 176/1 |
| 4,249,077 A | 2/1981 | Crawford | |
| 5,798,529 A | * 8/1998 | Wagner | 250/492 |
| 6,114,695 A | * 9/2000 | Todokoro | 250/310 |

OTHER PUBLICATIONS

Introduction of Analytical Electron Microscopy—Chapter 18, pp. 481–505, Barriers to AEM: Contamination of Etching, J.J. Hren, Dept. of Material s Science and Engineering University of Florida Gainesville, Forida.

Performance of gas assist FIB repair for opaque defects, Yasushi Satoh, Hiroshi Nakamura, Junji kawa, Katsuhide Tsuchiya, Shigeru Noguchi, Kazuo Aita, Anto Yasaka; 124–137/SPIE vol. 2884.

$H_2O$ enhanced focused ion beam micromachining, T.J. Stark, et al., N.C. State Univ., 2565–2569, J. Vac. Sci.Tehnol. B 13(6) Nov./Dec. 1995.

Water–Based Antistatic Coating of Photomasks, Micron Applications Lab., PR–107, Jan. 11, 1989, John Morgan.

* cited by examiner

Primary Examiner—John R. Lee
Assistant Examiner—Anthony Quash
(74) Attorney, Agent, or Firm—Dickstein Shapiro Morin & Oshinsky LLP

(57) ABSTRACT

A method and apparatus for reducing the charging effect of electron beam devices on non-conducting samples includes introducing a water containing gas on the sample surface. Because the water containing gas is conductive, the charge is dissipated. The water containing gas may be introduced by a nozzle and the pressure may be adjusted to provide an amount of water containing gas sufficient to dissipate the charging effect produced by the electron beam. In a preferred embodiment, the water containing gas is water vapor. This technique is especially useful for inspection of quartz samples such as quartz photomasks with scanning electron microscopes because water vapor exhibits good adhesion to quartz surfaces, which helps to distribute and dissipate the charge quickly. A method for reducing carbon deposition caused by an electron beam device also involves introducing a water containing gas on the sample surface. This method is effective for both conductive and non-conductive samples.

23 Claims, 1 Drawing Sheet

REDUCTION OF CHARGING EFFECT AND CARBON DEPOSITION CAUSED BY ELECTRON BEAM DEVICES

BACKGROUND OF THE INVENTION

1. Field of the Invention

The present invention relates generally to the field of electron beam devices and more particularly to the reduction of the charging effect on a non-conductive sample and reduction of carbon deposition on samples.

2. Description of the Related Art

This invention is primarily directed toward devices which emit an electron beam over a target. Such devices are referred to herein as electron beam devices. An important example of such a device is a scanning electron microscope, which shall be referred to herein as a SEM. Electron lithography systems and electron microprobes are among other devices employing electron beams.

In a SEM, an electron beam is swept over a target and electrons that "bounce" off the target are collected to generate a signal representing the topographical features of the target. Both the electron beam and the sample are inside a vacuum chamber. The electrons may be back-scattered primary electrons (those electrons which are reflected back along the path they traveled during emission) or secondary electrons (electrons which are generated upon target impact). The resolution of the SEM depends in part upon the narrowness of the electron beam and the accuracy with which the beam position is controlled during the scanning operation.

When the sample to be imaged has a non-conducting surface, there is a build up of a negative charge on the sample due to the electron beam. The negative charge diverts the beam (causing a decreased beam positioning accuracy) and causes the beam to widen. Both of these effects reduce the accuracy of the SEM. An analogous problem exists in electron beam lithography processes. Such effects are referred to herein as "charging effects."

One known solution to this problem is to coat the surface of the sample with a thin conductive layer. For example, use of such a coating is discussed in U.S. Pat. No. 4,249,077, entitled "ION CHARGE NEUTRALIZATION FOR ELECTRON BEAM DEVICES." A second known solution involves emitting positive ions into the vacuum chamber in an attempt to neutralize the charge on the sample. This technique is also described in U.S. Pat. No. 4,249,077. Another attempted solution to this problem is to keep the intensity of the electron beam low and to keep the scan time short in order to minimize the charge that is built up on the sample. The aforementioned solutions have not proven satisfactory. They involve increased cost, complexity and/or time or are simply not sufficiently effective.

The charging effect has become a particularly serious problem in the semiconductor manufacturing field. Quartz, a non-conducting material, is often used as a substrate for masks used in photo and x-ray lithography processes. Optical microscopes have traditionally been used to review masks for defects (such as divot or bump defects on a phase shift mask and opaque and clear defects on a Cr mask) and to measure critical dimensions of masks. However, with the mask feature size now reaching the submicron level (i.e. less than 0.5 microns), optical measurements have proven inadequate. Therefore, the semiconductor industry has turned to SEMs as an alternative to optical microscopes. This reliance on SEMs for quartz mask inspection has served to highlight the deficiencies of the aforementioned techniques for reducing the charging effect on non-conductive samples.

A second, well known phenomena associated with electron beam use in general and SEMs in particular is carbon deposition, including carbon film and carbon halos, in the area near the electron beam (the image window area in a SEM). Carbon deposits may form on conductive as well as non-conductive samples. The carbon deposit is formed by electron beam bombardment of residual organic molecules inside the vacuum chamber from sources such as improperly handled samples, vacuum pump grease, etc. Although the use of proper sample handling procedures and advances in vacuum pump technology can help to reduce the amount of organic residue, to date the total elimination of organic residue is not yet possible and would most likely be prohibitively expensive even if it were. Carbon deposition adversely affects mask quality, and may cause shorts or may cause the rejection of the mask.

What is needed is a simple, inexpensive way to reduce the charging effect of electron beam devices on non-conducting samples and to reduce carbon deposition on samples of all types.

SUMMARY OF THE INVENTION

The present invention provides a method for reducing the charging effect of electron beam devices on non-conducting samples that involves introducing a water containing gas on the sample surface while the electron beam is directed on the sample. Because the water containing gas is conductive, the charge is dissipated. The water containing gas may be introduced with an adjustable nozzle and the pressure at which the gas is provided may be adjusted to provide an amount of water containing gas sufficient to dissipate the charging effect produced by the electron beam. In a preferred embodiment, the water containing gas is water vapor and the water vapor is introduced continuously. This technique is especially useful for quartz samples such as quartz photomasks because water vapor exhibits good adhesion to quartz surfaces, which helps to distribute and dissipate the charge quickly.

A second advantage of introducing water containing gas is that carbon deposits can be minimized. When a water containing gas is present, carbon monoxide or carbon dioxide is formed as the residual organic molecules react with the water molecules contained in the gas. This benefit may be realized with both conductive and non-conductive samples.

The use of water vapor to increase the material removal rates in chemically enhanced focused ion beam micro-machining is described in "$H_2O$ Enhanced Focused Ion Beam Micro-machining," Stark et al., J. Vac. Sci. Technol. B 13(6), November/December 1995, p. 2565. Furthermore, the use of a water containing gas to enhance the removal rate of a carbon halo formed on a photomask during a clear defect repair with a focused ion beam is described in my co-pending application entitled "Method for Removing the Carbon Halo Caused by FIB Clear Defect Repair of a Photomask," Ser. No. 09/190057, filed Nov. 12, 1998. However, the applicant is not aware of any information that teaches use of a water containing gas to reduce the charging effect on non-conductive samples or to retard the formation of carbon deposits during exposure to electron beams or focused ion beams.

BRIEF DESCRIPTION OF THE DRAWING

The foregoing and other advantages and features of the invention will become more apparent from the detailed description of the preferred embodiments of the invention given below with reference to the accompanying drawing in which.

DETAILED DESCRIPTION OF THE PREFERRED EMBODIMENTS

Figure 1:
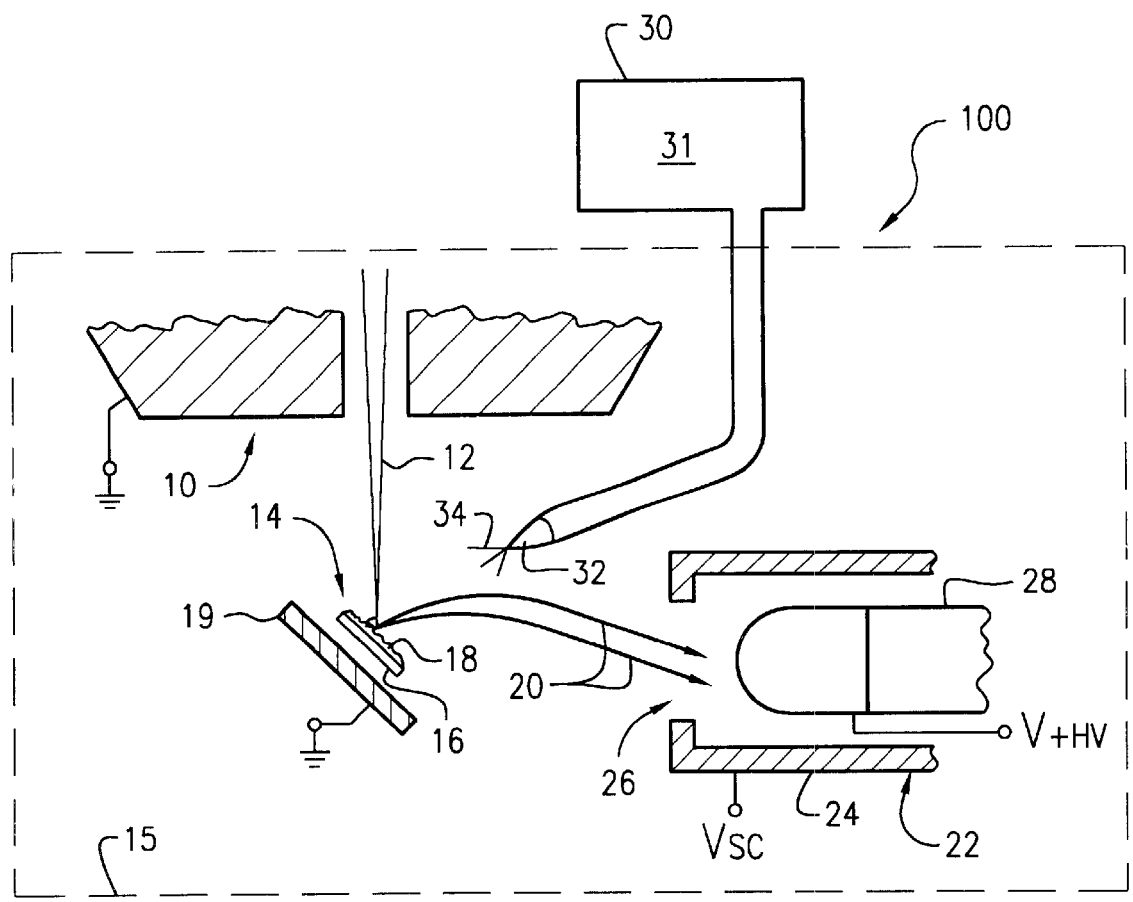
FIG. 1 is a schematic diagram of a SEM including a water containing gas injection device in accordance with the present invention.

The present invention will be illustrated through a description of a scanning electron microscope and gas injection nozzle. Specific details, such as distances and measurements, are set forth in order to provide a thorough understanding of the present invention. It will be obvious, however, to one skilled in the art that the present invention is capable of many different embodiments and that the present invention may be practiced without using the specific details of the exemplary embodiment. Accordingly, the drawing and description herein are to be regarded as illustrative in nature and not as restrictive.

A schematic view of a portion of a SEM 100 according to one embodiment of the present invention is shown in FIG. 1. The SEM 100 includes an electron beam generating and scanning assembly 10, which focuses and scans an electron beam 12 over a target 14. The target 14 includes both a conductive substrate 16 and a sample 18 mounted thereon. Although the substrate 16 is shown spaced apart from a ground plate 19 in FIG. 1, in reality the substrate 16 is in electrical contact with the ground plate 19. When the sample 18 is conductive, any charge on the sample 18 is dissipated through the path from the sample 18 to the substrate 16 to the ground plate 18. However, when the sample is non-conductive, the electrons cannot be dissipated in this manner. The sample is enclosed in a vacuum chamber represented schematically as element 15 of FIG. 1.

As the beam 12 impacts the sample 14, both primary and secondary electrons 20 are reflected. The electrons 20 are attracted to a detector 22 by an electrode 24. The electrode is maintained at a suitable positive voltage to attract the electrons 20. The electrons 20 pass through an opening 26 to a collector 28, which is maintained at a suitable higher positive voltage than the electrode 24. Because of the limited efficiency of back scattering and secondary electron generation the number of electrons 20 leaving the sample 18 is less than the number of electrons in the beam 12, which results in a net negative charge build up on the sample 18.

The SEM 100 includes a gas injector 30 including a reservoir 31 and an adjustable nozzle 32. The reservoir 31 contains a supply of water containing gas. The gas injector 30 is used to inject a water containing gas 34 into the vacuum chamber toward the sample 18. The opening of the nozzle 32 and the distance of the nozzle 32 from the sample 18 are adjusted to deliver the water containing gas 34 at an appropriate rate depending upon the intensity of the electron beam 12. When the water containing gas 34 is introduced into the chamber 15, the pressure inside the chamber is maintained between approximately $10^{-6}$ and $10^{-5}$ torr. Experience has shown that, for a sample consisting of an average size mask and an electron beam intensity of approximately 1000–2000 electron-Volts, a nozzle opening of approximately 200 to 500 microns is appropriate for a nozzle-to-sample distance of approximately 1 to 2 millimeters and a supply of pure water vapor which is held in the reservoir 31 at slightly below room temperature at approximately 1 torr background pressure.

The water molecules from the water containing gas 30 exhibit good adherence to the surface of the sample 18, which aids charge dissipation on the sample 18 since the water molecules are charge conductive. The charge is dissipated through the water molecules on the surface of the sample 18 to the substrate 16 to the ground plate 19.

The water containing gas 34 is continuously output by the gas injector 30 whenever the electron beam 12 is active in the preferred embodiment, although this is not absolutely necessary. The water containing gas 34 is water vapor in the preferred embodiment, although other water containing gases are also possible. It is preferable that the gas used have a water vapor content of 90% or greater, although the use of gases with lesser amounts of water vapor is also possible. If water vapor is used, the temperature of the reservoir 31 is kept at or slightly above or below room temperature. If other gases are used, it may be necessary to increase or decrease the temperature of the reservoir 31 above or below room temperature to ensure that a sufficient amount of water molecules are available at the surface of the sample 18. The actual temperature and pressure of the water containing gas supply and nozzle adjustment are dependent upon a number of factors including the intensity of the electron beam, the vacuum chamber pressure, and the actual composition of the water containing gas. The necessary adjustments will be apparent to those of ordinary skill in the art.

As a result of electron bombardment the water molecules also reduce the formation of carbon films or halos by reacting with any residual organic molecules in the vacuum chamber to form carbon monoxide or carbon dioxide. As mentioned above, the carbon deposit reduction effect may be realized for both conductive and non-conductive samples.

Thus, the present invention provides a method and apparatus for both reducing the charging effect on non-conductive samples and for reducing carbon deposition on both conductive and non-conductive samples through the introduction of a water containing gas on the sample surface.

While the invention has been described in detail in connection with the preferred embodiments known at the time, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Accordingly, the invention is not to be seen as limited by the foregoing description, but is only limited by the scope of the appended claims.

What is claimed as new and desired to be protected by Letters Patent of the United States is:

1. A method for reducing the charging effect caused by the exposure of a non-conductive sample to an electron beam, the method comprising the step of:
   introducing a water containing gas onto a surface of the sample while the electron beam is present to provide an electrical path through water deposited on the sample for discharging a charge from the sample.

2. The method of claim 1, wherein the water containing gas contains at least 90% water vapor.

3. The method of claim 2, wherein the water containing gas consists of water vapor.

4. The method of claim 1, wherein the water containing gas is introduced continuously while the sample is in the presence of the electron beam.

5. The method of claim 1, wherein the temperature of the water containing gas is kept slightly below room temperature.

6. The method of claim 1, wherein the electron beam is produced by an electron microscope.

7. The method of claim 1, wherein the introducing step is performed by positioning a nozzle of a water containing gas device approximately one to two millimeters from the surface and adjusting an opening of the nozzle to approximately 200 to 500 microns.

8. A method for reducing the formation of carbon deposits on a sample caused by exposure of the sample to an electron beam, the method comprising the step of:

introducing a water containing gas onto a surface of the sample while the electron beam is present to provide water molecules to react with residual organic molecules in order to reduce the formation of carbon deposits.

9. The method of claim 8, wherein the water containing gas contains at least 90% water vapor.

10. The method of claim 8, wherein the water containing gas consists of water vapor.

11. The method of claim 8, wherein the water containing gas is introduced continuously while the sample is in the presence of the electron beam.

12. The method of claim 8, wherein the temperature of the water containing gas is kept slightly below room temperature.

13. The method of claim 8, wherein the electron beam device is an electron microscope.

14. The method of claim 8, wherein the introducing step is performed by positioning a nozzle of a water containing gas device approximately one to two millimeters from the surface and adjusting an opening of the nozzle to approximately 200 to 500 microns.

15. An electron beam device for exposing a sample to an electron beam, the electron beam device comprising:

a vacuum chamber;

a grounded plate positioned inside the vacuum chamber, said plate being adapted to engage a sample;

an electron beam generator for generating an electron beam inside the vacuum chamber and directing the electron beam toward the sample; and a gas injector connectable to a supply of water containing gas for injecting the water containing gas into the vacuum chamber onto a surface of the sample to provide an electrical path through water deposited on the sample for discharging a charge from the sample while the electron beam is present.

16. The device of claim 15, wherein the water containing gas provides an electrical path through water deposited on the sample for discharging a charge on the sample.

17. The device of claim 15, wherein the water containing gas provides water molecules to react with residual organic molecules in order to reduce the formation of carbon deposits.

18. The device of claim 15, wherein the water containing gas contains at least 90% water vapor.

19. The device of claim 15, wherein the water containing gas consists of water vapor.

20. The device of claim 15, wherein the water vapor gas is introduced continuously while the sample is in the presence of the electron beam.

21. The device of claim 15, further comprising means for maintaining the temperature of the water containing gas slightly below room temperature.

22. The device of claim 15, wherein the device further comprises means for scanning the electron beam across the target.

23. The device of claim 15, wherein the gas injector includes an adjustable nozzle and a position of the nozzle with respect to the sample is adjustable.

* * * * *